(12) United States Patent
Sweis et al.

(10) Patent No.: US 11,123,140 B1
(45) Date of Patent: Sep. 21, 2021

(54) COMPUTING PLATFORM FOR IMPROVED AESTHETIC OUTCOMES AND PATIENT SAFETY IN MEDICAL AND SURGICAL COSMETIC PROCEDURES

(71) Applicants: Iliana E. Sweis, Chicago, IL (US); Bryan C. Cressey, Chicago, IL (US)

(72) Inventors: Iliana E. Sweis, Chicago, IL (US); Bryan C. Cressey, Chicago, IL (US)

( * ) Notice: Subject to any disclaimer, the term of this patent is extended or adjusted under 35 U.S.C. 154(b) by 148 days.

(21) Appl. No.: 16/399,916

(22) Filed: Apr. 30, 2019

Related U.S. Application Data

(60) Provisional application No. 62/664,903, filed on Apr. 30, 2018.

(51) Int. Cl.
*A61B 34/10* (2016.01)
*G16H 50/50* (2018.01)
*G16H 30/40* (2018.01)
*G16H 20/40* (2018.01)
*G16H 80/00* (2018.01)

(52) U.S. Cl.
CPC .............. *A61B 34/10* (2016.02); *G16H 30/40* (2018.01); *G16H 50/50* (2018.01); *A61B 2034/101* (2016.02); *G16H 20/40* (2018.01); *G16H 80/00* (2018.01)

(58) Field of Classification Search
CPC .......... A61B 2017/00792; A61B 34/10; A61B 2017/00747; A61B 2018/0047; G16H 50/50; G16H 50/20; G16H 30/20; G16H 50/30
See application file for complete search history.

(56) References Cited

U.S. PATENT DOCUMENTS

| 7,713,234 B2 | 5/2010 | Karanzas |
| 8,075,525 B2 | 12/2011 | Yang |
| 8,133,201 B1 | 3/2012 | Hurtado |
| 2004/0153031 A1 | 8/2004 | Van Kaauwen |
| 2005/0148935 A1 | 7/2005 | Dimitrova et al. |
| 2010/0015590 A1 | 1/2010 | Kiss |

(Continued)

FOREIGN PATENT DOCUMENTS

| WO | WO2015/085019 | 6/2015 | |
| WO | WO-2017151963 A1 * | 9/2017 | ............. A61B 34/20 |

OTHER PUBLICATIONS

Chang, Chuan-Yu, et al. "Automatic facial skin defect detection system." 2010 International Conference on Broadband, Wireless Computing, Communication and Applications. IEEE, 2010. (Year: 2010).*

(Continued)

*Primary Examiner* — Elaine Gort
*Assistant Examiner* — Constantine B Siozopoulos
(74) *Attorney, Agent, or Firm* — Morgan, Lewis & Bockius LLP

(57) ABSTRACT

An electronic computing system creates a treatment plan and provides safe and accurate treatment recommendations by obtaining an input image of a face; comparing, using a pattern recognition process, one or more aspects of the input image to corresponding aspects of a plurality of reference images; obtaining, based on a result of the comparing, supplemental information associated with one or more additional characteristics of the face; and creating a treatment plan based on the input image and the additional characteristic.

17 Claims, 7 Drawing Sheets

(56) References Cited

U.S. PATENT DOCUMENTS

| | | |
|---|---|---|
| 2013/0231583 A1 | 9/2013 | Rekkerth |
| 2014/0039658 A1 | 2/2014 | Bangera et al. |
| 2014/0121637 A1* | 5/2014 | Boyden ................ A61M 5/427 |
| | | 604/506 |
| 2014/0257183 A1 | 9/2014 | Mica et al. |
| 2015/0339757 A1* | 11/2015 | Aarabi .................. G06Q 30/06 |
| | | 705/12 |

OTHER PUBLICATIONS

Sweis, Office Action, U.S. Appl. No. 15/162,952, dated Jun. 14, 2018, 9 pgs.

Sweis, Final Office Action, U.S. Appl No. 15/162,952, dated Oct. 18, 2018, 9 pgs.

Sweis, Office Action, U.S. Appl. No. 15/162,952, dated Jan. 11, 2019, 8 pgs.

Sweis, Notice of Allowance, U.S. Appl. No. 15/162,952, dated Apr. 23, 2019, 7 pgs.

\* cited by examiner

| Treatment Data 200 | | |
|---|---|---|
| Image 126a | Data 128a<br>-Outcome<br>-Information | Treatment 130a<br>-Step 1<br>-Step 2<br>-Step 3 |

Figure 2

| Validation Data 300 | | |
|---|---|---|
| Image 302a | Decision 304a<br>-Invalid | Direction 306a<br>-Look down |
| Image 302b | Decision 304b<br>-Invalid | Direction 306b<br>-Look straight |
| Image 302c | Decision 304c<br>-Valid | Direction 306c<br>-n/a |

Figure 3

| Evaluation Data 400 | | |
|---|---|---|
| Image 126a | Data 128a<br>-Outcome<br>-Information | Questions 406<br>-Question 1<br>-Question 2 |

Figure 4

| Anatomical Data 500 | | |
|---|---|---|
| Image 126a | Anatomy 502 | Anatomy 504 |

Figure 5

| Rating Data 600 | | |
|---|---|---|
| Image 602a | Beauty 604a -Score: 6 | Youth 606a -Score: 8 |
| Image 602b | Beauty 604b -Score: 2 | Youth 606b -Score: 5 |
| Image 602c | Beauty 604c -Score: 8 | Youth 606c -Score: 9 |

Figure 6

| Comparison Data 700 | | |
|---|---|---|
| Before 702 | Treatment 130a -Step 1 -Step 2 -Step 3 | After 704 |

Figure 7

COMPUTING PLATFORM FOR IMPROVED AESTHETIC OUTCOMES AND PATIENT SAFETY IN MEDICAL AND SURGICAL COSMETIC PROCEDURES

RELATED APPLICATIONS

This application claims priority to U.S. Provisional Patent Application 62/664,903, filed Apr. 30, 2018, entitled "Computing Platform for Improved Aesthetic Outcomes and Patient Safety in Cosmetic Procedures," which is hereby incorporated by reference in its entirety.

This application is related to U.S. patent application Ser. No. 15/162,952, filed May 24, 2016, entitled "Marking Template for Medical Injections, Surgical Procedures, or Medical Diagnostics and Methods of Using Same," which is hereby incorporated by reference in its entirety.

TECHNICAL FIELD

This application relates generally to computer technology and medical and/or surgical cosmetic procedures, including but not limited to methods and systems for using machine learning to improve aesthetic outcomes and patient safety.

BACKGROUND

There is a continuing increase in the number of medical and surgical cosmetic procedures being performed, the most significant of which is facial injectables. These include two main categories: neuromodulators and soft tissue fillers. The potential complications of soft tissue fillers are serious, and may be permanent. For instance, cases of stroke and blindness have been reported with the use of soft tissue fillers. The reported cases do not include cases that are performed under less than ideal conditions and go unreported.

There are core physicians who perform these injections, including plastic surgeons, dermatologists, facial plastic surgeons, and oculoplastic surgeons. These practitioners are considered to be properly trained injectors. Many physicians delegate the injections to nurses in their practice (nurse injectors) who have attended courses and learned to inject. In addition to the core physicians, many non-core physicians (internists, family practice, gynecologists, anesthesiologists, etc.) have opened medical spas and a significant portion of their business is injectables. More importantly, many injectors are not physicians or even nurses.

Due to the wide range of practitioner backgrounds in the field of cosmetic procedures, as well as the potential for serious complications, there is a need for improved aesthetic outcomes and increased safety of patients who are seeking such treatments.

SUMMARY

Implementations described in this specification are directed to providing a computing platform for use by medical providers who treat patients seeking cosmetic procedures. In some implementations, the platform stores and analyzes a plurality of images of faces (e.g., several thousand faces), and/or information associated with images of faces, and uses machine learning and/or pattern recognition (collectively, "machine learning") to create treatment plans and recommendations in order to (i) reduce errors for practitioners and (ii) achieve better outcomes for patients.

In one aspect of the application, a method of creating safe and accurate treatment plans is implemented at a computer system having one or more processors and memory storing one or more programs for execution by the one or more processors. The method includes obtaining an input image of a face; comparing, using a machine learning process, one or more aspects of the input image to corresponding aspects of a plurality of reference images; obtaining, based on a result of the comparing, supplemental information associated with one or more additional characteristics of the face; and creating a treatment plan based on the input image and the supplemental information.

In accordance with some aspects of this application, a computer system includes memory storing instructions for causing the computer system to perform any of the methods described herein.

Further, in accordance with some aspects of this application, instructions stored in memory of a computer system include instructions for causing the computer system to perform any of the methods described herein.

Other embodiments and advantages may be apparent to those skilled in the art in light of the descriptions and drawings in this specification.

BRIEF DESCRIPTION OF THE DRAWINGS

For a better understanding of the various described implementations, reference should be made to the Description of Implementations below, in conjunction with the following drawings in which like reference numerals refer to corresponding parts throughout the figures.

FIGS. 2-7 are diagrams illustrating data structures used by the machine learning module of FIG. 1, in accordance with some embodiments.

Like reference numerals refer to corresponding parts throughout the drawings.

DESCRIPTION OF IMPLEMENTATIONS

Figure 1:
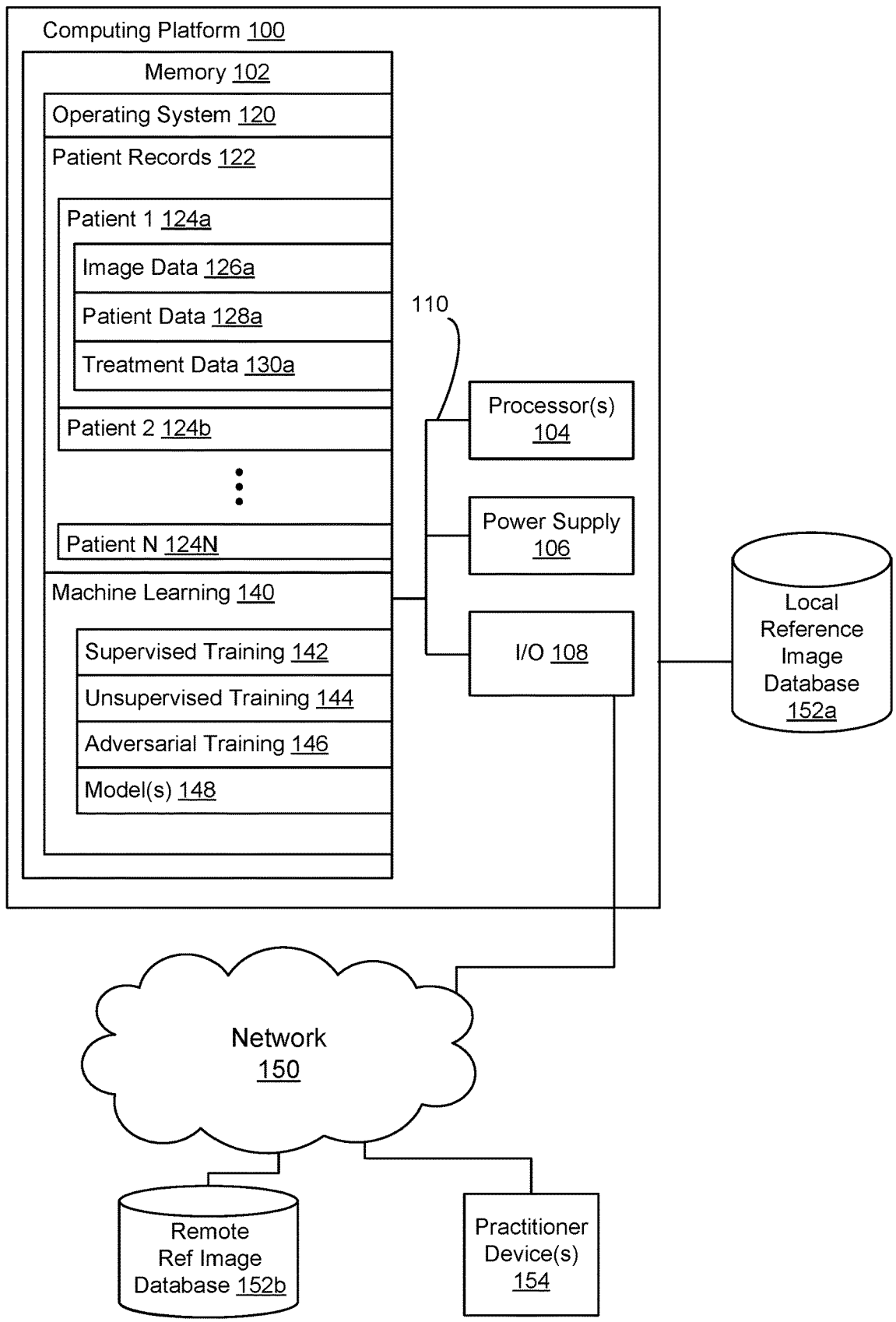
FIG. 1 is a system diagram of a computing platform and its context, in accordance with some embodiments.

Implementations described in this specification are directed to providing a computing platform for use by medical providers who treat patients seeking cosmetic procedures. In some implementations, the platform stores and analyzes a plurality of images of faces (e.g., several thousand faces), or information associated with images of faces, and uses machine learning to create treatment plans and recommendations in order to (i) reduce errors for practitioners and (ii) achieve better outcomes for patients.

The potential complications of neuromodulators, such as a droopy eyelid and facial asymmetry, are self-limiting and reversible. The neuromodulator effect usually diminishes by two months, and is usually gone by three months.

However, the potential complications of fillers are more serious, and may be permanent. This is due to the fact that these products are not water soluble. The facial blood supply is quite extensive and vessels communicate with one another through an arcade. It is possible for the needle to be accidentally placed through a blood vessel during injection, which could result in compromising the blood flow to the area supplied by that vessel. This may lead to a temporary change in color or in tissue death in the treated area leading to a scab and/or permanent scar formation. In some cases, the product can be carried in a vessel that reaches the brain or the eye, which may lead to a stroke or blindness.

The implementations described herein improve aesthetic outcomes and increase the safety of patients who are seeking such treatments. In some implementations, the computing platform achieves these outcomes by using machine learning, in combination with beauty and safety databases, facial topographical analysis, and multispecialty medical expertise to create treatment plans for patients seeking aesthetic improvements (e.g., to the face).

In some implementations, the computing platform utilizes visual sensors to gather facial data in order to develop facial recognition and further utilizes machine learning to understand concepts of facial youthfulness and facial beauty. The platform combines that data with topographical facial analysis and the expertise of a large group of plastic surgeons, dermatologists, and other cosmetic specialists to create and recommend safe treatment protocols and algorithms for enhancing the facial features according to documented, artistic and machine-learned concepts of youth and facial beauty.

In some implementations, the computing platform utilizes facial recognition and machine learning to determine whether or not the patient is a good candidate for injectables or whether surgery is a more appropriate option. In some implementations, the computing platform determines whether a patient is a proper candidate for elective procedures based on their answers to a preliminary evaluation (e.g., a questionnaire with a built-in scale assessing psychological stability and possible Body Dysmorphic Syndrome).

In some implementations, the knowledge base for the computing platform is initially provided by one or more of: plastic surgeons, facial plastic surgeons, oculoplastic surgeons, dermatologists, laser specialists, psychiatrists, anatomists, and/or research and development experts in the fields of neuromodulators and facial fillers.

In some implementations, the computing platform has at least two major subject areas for machine learning: (1) enhancing facial features (e.g., through injectables and/or surgery), and (2) reversing signs of aging (e.g., through injectables and/or surgery).

Embodiments of the computing platform disclosed herein increase the safety of injections being performed on the patient, improve the aesthetic quality and outcome of injections being performed on the patient, do not require a core facial aesthetic physician to implement, allow use by a nurse or doctor who is not a core facial aesthetic specialist, continue learning and adapt as new concepts of facial beauty evolve over time, and/or continue learning and adapt as new injectable products, new lasers, new skin care lines and/or new surgical procedures are developed.

Embodiments of the computing platform disclosed herein provide specific protocols using neuromodulators and soft tissue fillers with detailed guidance as to how to inject these in specific locations (e.g., facial locations) to obtain excellent aesthetic outcomes while promoting a high degree of patient safety by accounting for nerves, blood vessels and other vital structures. In some implementations, the computing platform provides recommendations for further skin enhancement using laser treatments and medical grade skin care.

In some implementations, a practitioner (e.g., nurse or doctor) uploads, or otherwise inputs, one or more photos of a patient's face. In some implementations, the computing platform first validates the image(s), for example, by indicating whether the image(s) meet a threshold level of quality and/or satisfy particular angles.

In some implementations, the computing platform analyzes the images to determine skin type (e.g., Fitzpatrick Classification (Type I through VI)) and/or specific details of the face and neck relative to documented and learned concepts of youth and facial beauty as defined within a particular race, ethnicity, gender, and/or age. For example, the computing platform analyzes one or more of:
   Facial Structure (e.g., adequate or deficient bone structure based on external bony landmarks, adequate or deficient soft tissue volume in upper third, mid-third and lower third of face);
   Rhytids due to muscle movement (e.g., with classification between dynamic rhytids and static rhytids);
   Rhytids due to loss of skin constituents (e.g., collagen, elastin and hyaluronic acid)
   Solar elastosis (e.g., percentage of face and neck affected by sun damage, solar lentigines, redness, prominent vessels), and/or
   Extent of descent of the superficial musculoaponeurotic system (SMAS), platysma, and overlying tissues.

In some implementations, the computing platform then analyzes the images to determine how to improve the face based on documented and learned concepts of facial beauty. For example, the computing platform utilizes 3D facial imaging, Smart Grid imaging (e.g., as disclosed in U.S. patent application Ser. No. 15/162,951, which is incorporated by reference in its entirety), and facial vessel visualization technology to outline the accurate and safe placement of soft tissue fillers in the face.

In some implementations, the computing platform instructs the injector step-by-step using neuromodulators and soft tissue filler injection techniques that implement a high degree of patient safety. For example, the computing platform identifies for the injector one or more of:
   Degree of difficulty of injection and level of injector experience required;
   Degree of patient satisfaction with particular injection procedures (e.g., high patient satisfaction; relatively predictable outcome; variable patient satisfaction; sometimes unpredictable outcome); and/or
   Risk of complications (e.g., low, medium, high)

In some implementations, the computing platform analyzes the image(s) to determine one or more of:
   What injection products to use;
   Where to place each of the injections (e.g., using Smart Grid imaging and/or vessel visualization technology);
   What the ideal sequence of injections is;
   How much product to use in each facial region or injection site;
   What depth of injection is safest in different facial regions;
   What technique of injection is necessary for each region; and/or
   Visualization of partial correction and complete correction of the face prior to performing the injections.

In some implementations, the computing platform performs one or more of the above determinations by:
   Identifying proper candidates for injectables;
   Identifying the most likely anatomy of the vessels, nerves, fat, facial muscles, bony structure, and parotid glands in the face;
   Recommending the proper neuromodulator and soft tissue filler for each area to be treated;
   Recommending the correct sequence of the injections;
   Recommending the proper volume of the injections;

Advising how to avoid pitfalls/complications;
Providing technique videos;
Demonstrating to the patient what multilevel injections can achieve at each level of injection (e.g., after a first injection, second injection, and so forth); and/or
Addressing the risks associated with each injection.

In some implementations, the computing platform performs a surgical evaluation of the face to determine a proper course of action with non-surgical procedures. For example, injectables may be used to get as close as possible to a surgical result. In some implementations, the computing platform evaluates one or more Aesthetic Facial Units in terms of what is deficient and what is in excess, what is missing and what is an undesirable trait (e.g., low lying eyebrows, deficient cheek bones, deficient chin projection, excess maxillary show, presence of jowls, etc.), and determines the proper treatment plan.

For example, instead of looking at wrinkles in the forehead to determine where and how much of an injectable to use to treat the wrinkles, the computing platform evaluates the forehead as a unit and examines the brow position, loss of volume, extent and location of wrinkles, and asymmetry. The computing platform then creates a treatment plan that includes recommending the proper dose and placement of one or more particular injectables, as well as the proper sequence of injection, to create a more aesthetic brow position and to soften the forehead wrinkles and restore volume (similar to what could alternatively be achieved through a surgical brow lift).

Applying a surgical approach to non-surgical techniques is unique in that it increases the safety and aesthetic results of current techniques. Stated another way, the computing platform dictates non-surgical treatment recommendations in a medical/surgical discipline.

In some implementations, the computing platform performs a surgical evaluation of various parts of the body to determine a proper course of action using surgical procedures. Example surgical procedures include surgery of the breast, nose shaping, and flap reconstruction. For each type of surgical procedure, the computing platform evaluates one or more physical characteristics (e.g., presented in images and/or alternative media), and creates and recommends one or more treatment plans as described below. To be clear, example processes described in this specification for creating and recommending treatment plans apply equally to surgical procedures as well as to non-surgical procedures.

While implementations described herein may refer to the face or regions surrounding the face (e.g., nose, neck), these references are exemplary in nature, and those skilled in the art will appreciate from the present disclosure that various other parts of the human body have not been illustrated for the sake of brevity, and so as not to obscure more pertinent aspects of the example implementations disclosed herein. As such, examples described herein referring to the face should be construed as also being applicable to any other part of the body.

Computing Platform Architecture

FIG. 1 is a system diagram of a computing platform 100 (also referred to herein as a "machine learning system"), in accordance with some embodiments. The computing platform 100 typically includes a memory 102, one or more processor(s) 104, a power supply 106, an input/output (I/O) subsystem 108, and a communication bus 110 for interconnecting these components.

The processor(s) 104 execute modules, programs, and/or instructions stored in the memory 102 and thereby perform processing operations.

In some embodiments, the memory 102 stores one or more programs (e.g., sets of instructions) and/or data structures, collectively referred to as "modules" herein. In some embodiments, the memory 102, or the non-transitory computer readable storage medium of the memory 102 stores the following programs, modules, and data structures, or a subset or superset thereof:
    an operating system 120;
    patient records 122, including data for individual patients 124, which includes image data 126 (e.g., one or more images of the patient's face), patient data 128 (e.g., evaluation data such as questionnaire answers, age, gender, expectations, desired outcomes, and so forth), and/or treatment data 130 (e.g., a recommended procedure to be performed in accordance with the patient's desired outcome and image data, as determined by the computing platform); and
    a machine learning module 140 that uses supervised training module 142, unsupervised training module 144, and/or adversarial training module 146 to generate one or more facial models 148 (e.g., by analyzing reference images corresponding to a plurality of faces and procedures).

The above identified modules (e.g., data structures and/or programs including sets of instructions) need not be implemented as separate software programs, procedures, or modules, and thus various subsets of these modules may be combined or otherwise re-arranged in various embodiments. In some embodiments, the memory 102 stores a subset of the modules identified above. In some embodiments, a local reference image database 152a and/or a remote reference image database 152b store a portion or all of one or more modules identified above. Furthermore, the memory 102 may store additional modules not described above. In some embodiments, the modules stored in the memory 102, or a non-transitory computer readable storage medium of the memory 102, provide instructions for implementing respective operations in the methods described below. In some embodiments, some or all of these modules may be implemented with specialized hardware circuits that subsume part or all of the module functionality. One or more of the above identified elements may be executed by one or more of the processor(s) 104. In some embodiments, one or more of the modules described with regard to the memory 102 is implemented in the memory of a practitioner device 154 and executed by processor(s) of the practitioner device 154.

In some embodiments, generating a facial model 148 includes generating a regression algorithm for prediction of continuous variables (e.g., perspective transformation of a reference image and/or a more complex transformation describing morphing of facial images.

In some embodiments, the I/O subsystem 108 communicatively couples the computing platform 100 to one or more devices, such as a local reference image database 152a, a remote reference image database 152b, and/or practitioner device(s) 154 via a communications network 150 and/or via a wired and/or wireless connection. In some embodiments, the communications network 150 is the Internet.

The communication bus 110 optionally includes circuitry (sometimes called a chipset) that interconnects and controls communications between system components.

Typically, a system for recommending treatment procedures includes a computing platform 100 that is communicatively connected to one or more practitioner devices 154

(e.g., via a network 150 and/or an I/O subsystem 108). In some embodiments, the system receives patient records 122 (e.g., from a practitioner device 154 that captures or otherwise receives an image of a patient 124). For example, the patient data includes an image 126 and additional data 128 corresponding to the patient (e.g., desired outcome data). Practitioner device 154 is, for example, a computing system or platform (e.g., a laptop, computer, physical access system, or a mobile device) of a doctor or nurse.

Training the Computing Platform

In some implementations, an image database 152 of the computing platform stores a plurality of images of faces (e.g., hundreds, thousands, or more), or information associated with images of faces. In some implementations, each image (or information associated with each image) in the database is associated with a treatment plan, including one or more of (1) specific agents and amounts/units that were used or would be used, (2) locations for each injection, and (3) a proper sequence of injection, as described above. In some implementations, the treatment plans that are associated with each facial image correspond with actual treatment plans that were performed on the subject of the image. Alternatively, the treatment plans that are associated with each facial image correspond with suggested treatment plans, wherein the suggestions are based on various physical aspects of the face, such as shapes of facial features, positions of facial features with respect to other features, and/or locations of anatomical obstructions (e.g., nerves and blood vessels).

In some implementations, machine learning is used to identify commonalities in certain types of facial features in the context of their associated treatment plans. In other words, by using machine learning, the computing platform recognizes relationships between facial features and particular aspects of treatment plans. In some implementations, machine learning is applied to these relationships to extend the computing platform's basis for determining a treatment plan (also referred to herein as creating, generating, forming, or building a treatment plan) and making recommendations in accordance with the determined treatment plan. For example, the computing platform's basis for determining a treatment plan is extended to images of faces that have not been analyzed at the time of the treatment plan determination (referred to herein as new faces). As such, upon analyzing a new face, the computing platform identifies the most likely set of steps or processes for treatment of the new face based on the previously identified relationships between facial features in common with particular faces stored in the database and treatment plans corresponding to those particular faces.

In some implementations, in order to respect patient privacy, the computing platform deletes raw patient images after the platform has developed algorithms or models for creating treatment plans. Alternatively, in order to respect patient privacy, the facial images that are used for training are not obtained from patients, and instead are obtained from other sources (e.g., an online face repository).

In some implementations, facial images in the database are associated with "after" versions (which are also stored in the database) showing what the face looks like, or would look like, upon completion of treatment. In some implementations, the "after" image of a patient's face is obtained upon completion of an actual treatment. Alternatively, facial images obtained from non-patient sources are edited to show an "after" version of what the face would look like after a particular treatment procedure. Regardless of the source, the "after" images are stored in the database and are associated with the "before" images in the database, and the computing platform uses machine learning to determine what a new face would look like upon completion of a particular treatment procedure. In some implementations, the determined "after" image for a new face is displayed to the patient for the patient's consideration in electing whether to proceed with the particular treatment plan. In some implementations, the determined "after" image for a new face is displayed to the practitioner in order to assist the practitioner in carrying out the particular treatment plan, or in order to assist the practitioner in recommending alternative treatment plans.

In some implementations, the computing platform also considers, in addition to facial features, one or more additional characteristics associated with the face (or associated with the patient to which the face belongs; e.g., patient data 128), where the one or more additional characteristics are selected from the group consisting of: gender, age, concerns, goals, and physical conditions of various aspects of the face. In some implementations, these additional characteristics are also stored in the database and associated with each face, and the computing platform uses machine learning to recognize patterns and relationships between the faces and the additional characteristics.

In some implementations, the computing platform develops a plurality of base algorithms, directed to each additional characteristic, for creating treatment plans. Patients may present individual characteristics on a gradient. For example, for age: not too young, not too old, but somewhere in the middle; for goals: not too aggressive of a procedure, not too passive of a procedure, but somewhere in the middle; and so forth. Accordingly, in some implementations, the computing platform merges one or more of the base algorithms into a combined algorithm based on the gradients of the base algorithms. In other words, the combined algorithm creates a treatment plan based on a gradient of each base algorithm's treatment plan.

FIGS. 2-7 are diagrams showing data structures for machine learning processes in accordance with some embodiments. Embodiments of the machine learning module 140 train one or more facial models 148 in accordance with each figure, as explained in more detail below. In some embodiments, the image data and/or other data that make up the respective data structures is stored in a local or remote database 152. Alternatively, the image and/or other data that make up the respective data structures is stored in memory 102 of the computing platform 100. In any case, the computing platform inputs the data in a respective structure into a training module (e.g., 142, 144, or 146) for development of a respective model 148, as described below.

FIG. 2 is a diagram of treatment data 200 corresponding with patient 124a in FIG. 1 in accordance with some embodiments. For each patient, an image 126 (alternatively referred to herein as image data 126) is stored, along with non-image data 128 such as desired outcomes, patient expectations, physical characteristics of the patient (e.g., age, gender, and so forth), and/or anatomical information. When training a treatment model 148 for determining a recommended procedure for the particular patient, treatment data 130 is also stored and associated with the image 126 and data 128. In some embodiments, image data 126 includes a plurality of images of the patient, including images taken from different angles, and/or images showing different areas of the face. For training purposes, the image data 126 and non-image data 128 serve as a machine learning input, and the corresponding treatment data 130 serves as an input label for that machine learning input. With a set of inputs (e.g., hundreds, thousands, or more), machine learning module 140 generates a treatment model 148 for determining a treatment plan 130 for new sets of images 126 and data 128.

FIG. 3 is a diagram of validation data 300 corresponding with patient 124*a* in FIG. 1 in accordance with some embodiments. For each patient, image data 302 is stored, along with a validation decision (e.g., valid or invalid). The decision is based on the angles and areas necessary to be included in an image for a given procedure (described in more detail below). For training purposes, each image constituting image data 302 serves as machine learning input, and the corresponding validation decision 304 serves as an input label for that machine learning input. With a set of inputs, machine learning module 140 generates a validation model 148 for determining whether a subsequently received image is valid. Optionally, directions 306 are also included as input labels for training purposes. Accordingly, the validation model 148 would determine (i) whether a subsequently received image is valid, and (ii) if invalid, the reason the image was invalid. For example, in FIG. 3, the validation model determines that image 302*a* is invalid (304*a*) because certain facial features are not depicted in the expected locations with respect to one another. The validation model determines that if the patient tilts his or her head downward (306*a*), upward, to the left, or to the right, a subsequent image would likely produce a more useful result.

FIG. 4 is a diagram of evaluation data 400 corresponding with patient 124*a* in FIG. 1 in accordance with some embodiments. For each patient, image data 126 and non-image data 128 are stored as described above. For training purposes, image data 126 and non-image data 128 for the patient serves as a machine learning input, and one or more corresponding evaluation questions 406 (described in more detail below) serve as input label(s) 406 for that machine learning input. With a set of inputs, machine learning module 140 generates an evaluation model 148 for determining a set of evaluation questions to propose to the patient based on his or her image data 126 and non-image data 128. In some embodiments, training also includes an additional step (not shown), wherein the image data 126, non-image data 128, and responses to the questions 406 serve as machine learning inputs, and one or more additional questions serve as input label(s) for that machine learning input. As such, the evaluation model would first output an initial set of questions based on the image data 126 and non-image data 128, and responses to the initial set of questions would serve as an input to a secondary evaluation model, which would output a subsequent set of questions based on the responses to the initial set of questions. In some embodiments, depending on the complexity of the evaluation, additional steps are implemented as described above, from which successive sets of questions are generated based on responses to the prior questions.

FIG. 5 is a diagram of anatomical data 500 corresponding with patient 124*a* in FIG. 1 in accordance with some embodiments. For each patient, image data 126 is stored as described above. For training purposes, image data 126 serves as a machine learning input, and anatomical data (e.g., one or more anatomy images 502 and/or 504) serves as input label(s) for that machine learning input. With a set of inputs, machine learning module 140 generates an anatomical model 148 for determining anatomical data (described in more detail below) associated with the patient based on the patient's image data 126. Optionally, non-image data 128 also serves as machine learning input.

FIG. 6 is a diagram of rating data 600 corresponding to several example input images in accordance with some embodiments. For each input image 602, a beauty score 604 and/or a youth score 606 (each described in more detail below) are assigned. For training purposes, each image 602 serves as a machine learning input, and the beauty 604 and/or youth 606 scores serve as input label(s) for that machine learning input. With a set of inputs, machine learning module 140 generates an anatomical model 148 for assigning beauty and/or youth scores associated with input images. In some embodiments, the scores are included in the non-image data 128 for a patient and included as inputs in the treatment model (FIG. 2).

FIG. 7 is a diagram of comparison data 700 corresponding with patient 124*a* in FIG. 1 in accordance with some embodiments. For each patient, image data 702 from before a particular procedure (e.g., treatment plan 130) is stored as described above. Additional image data 704 of the patient is stored after the procedure (e.g., immediately after the procedure, or after an appropriate recovery period). For training purposes, a "before" image 702 and corresponding treatment data 130 serve as a machine learning input, and an "after" image 704 serves as an input label for that machine learning input. With a set of inputs, machine learning module 140 generates a comparison model 148 for predicting what a patient will look like (704) after having undergone a particular procedure. Alternatively, a "before" image 702 and a requested outcome (e.g., a specific facial change, such as larger cheekbones, as stored in data 128) serve as a machine learning input, and an "after" image 704 serves as an input label for that machine learning input. That way, a patient may request a particular procedure, and the computing platform displays an image of the patient that projects what the patient will look like after having completed the procedure, based on the comparison model 148.

For each of the machine learning diagrams described above, machine learning module develops respective models 148 using supervised training (142), unsupervised training (144), and/or adversarial training (146). For supervised training, a practitioner manually assigns labels for respective inputs. For example, a practitioner:

assigns a particular treatment plan 130*a* for patient 126*a* according to the image data 126 and data 128 for that patient (FIG. 2);

assigns validation decisions 304 and corresponding directions 306 based on various input images 302 (FIG. 3);

determines appropriate questions and/or evaluation steps 406 to take based on image data 126 and/or non-image data 128 of a patient (FIG. 4);

predicts various anatomical obstructions and adds indicators of those obstructions to anatomical images 502/504 for a particular patient 126 (FIG. 5);

assigns beauty 604 and/or youth 606 scores for various images of patients and/or nonpatients 602, such people whose faces represent societal norms of beauty and/or youth (FIG. 6); and/or chooses representative "after" images 704 for patients who have undergone particular procedures 130 (FIG. 7).

In some embodiments, supervised training module 142 facilitates manual labeling (as described above) by displaying successive input images to a practitioner (e.g., on a display on practitioner device 154), and receiving the manually entered input labels (e.g., from an input device via I/O module 108).

In some embodiments, after an initial learning process is complete, and models have been trained based on a plurality of inputs and corresponding labels, unsupervised training module 144 and/or adversarial training module 146 continue the training process by refining the models based on subsequently obtained images and data. In some embodiments, the computing platform obtains the subsequent images and data from an external source, such as an image gallery on the Internet. In some embodiments, training modules 144 and/or 146 periodically use subsequently obtained patient images to refine the models 148.

In some embodiments, machine learning module stores the input data and input labels as a pair (x, y), wherein x is the input data and y is the label. For some of the training embodiments described above, however, there are two or more inputs, or there are two or more labels. For these embodiments, the machine learning module trains the various models using a tuple $(x_1, x_2, y)$ for embodiments with multiple input fields (e.g., image data and non-image data). The machine learning module trains the various models using a tuple $(x, y_1, y_2)$ for embodiments with multiple labels (e.g., beauty score and youth score). Those skilled in the art will appreciate from the present disclosure that various other combinations of input (x) and label (y) data may be used by the machine learning module, depending on the training application. These other combinations have not been illustrated for the sake of brevity, and so as not to obscure more pertinent aspects of the example implementations disclosed herein.

Treatment Plan Creation

In some implementations, an image of the patient's face or other portion of the user's body is uploaded to the computing platform, the computing platform creates one or more treatment plans 130, and presents one or more treatment recommendations based on the one or more treatment plans 130. In some implementations, the treatment plans include: (1) one or more specific agents and amounts/units to inject, (2) the locations for each injection, and (3) the sequence of injection (the order in which individual injections should take place). In some implementations, the computing platform also displays an "after" image of the patient's face (or other body portion), detailing what the patient's face (or other body portion) is predicted to look like after the procedure.

In some implementations, the computing platform obtains additional information associated with the patient (e.g., by asking questions, displaying prompts, and so forth). The substance of the questions and the order of the questions depend on the facial features and answers to previous questions. In some implementations, a first question seeks to determine the patient's concerns and/or goals, and a second question seeks to determine if the patient has a particular physical condition associated with an area that the patient wants to be treated. Treatment plans may be influenced by answers to these questions.

In one example, the patient's goal is to treat forehead lines. In accordance with the patient's goal, the computing platform asks a question relevant to possible treatment options. In this scenario, the computing platform may ask if the patient has *frontalis* hyperactivity. If the answer is yes, the computing platform determines that the patient's forehead lines cannot be treated because treatment would result in a dropping of the brow. On the other hand, if the answer is no, the computing platform determines that the patient's forehead lines can be treated. In addition, the computing platform creates and recommends a specific treatment plan as described above, and, optionally, displays an "after" image for the patient to consider before electing to pursue the treatment plan.

In some implementations, subsequent prompts for additional treatment are displayed based on previous treatment areas. For example, the computing platform may determine that patients who elect to receive forehead line treatment usually also elect to receive eyelid treatment, and accordingly, the computing platform asks whether the patient would be interested in recommendations for eyelid treatment plans. In some implementations, one or more "after" images are constructed and displayed to the patient and/or the practitioner in order to assist in these treatment decisions.

In some implementations, from the patient's and/or the practitioner's point of view, the various implementations described herein demonstrate (1) the patient's current condition (e.g., what the patient looks like) at the time of consultation, (2) what the patient can look like after one or more customized treatment plans, and (3) the exact steps that would need to be taken in order to safely and accurately treat the patient.

Figure 8:
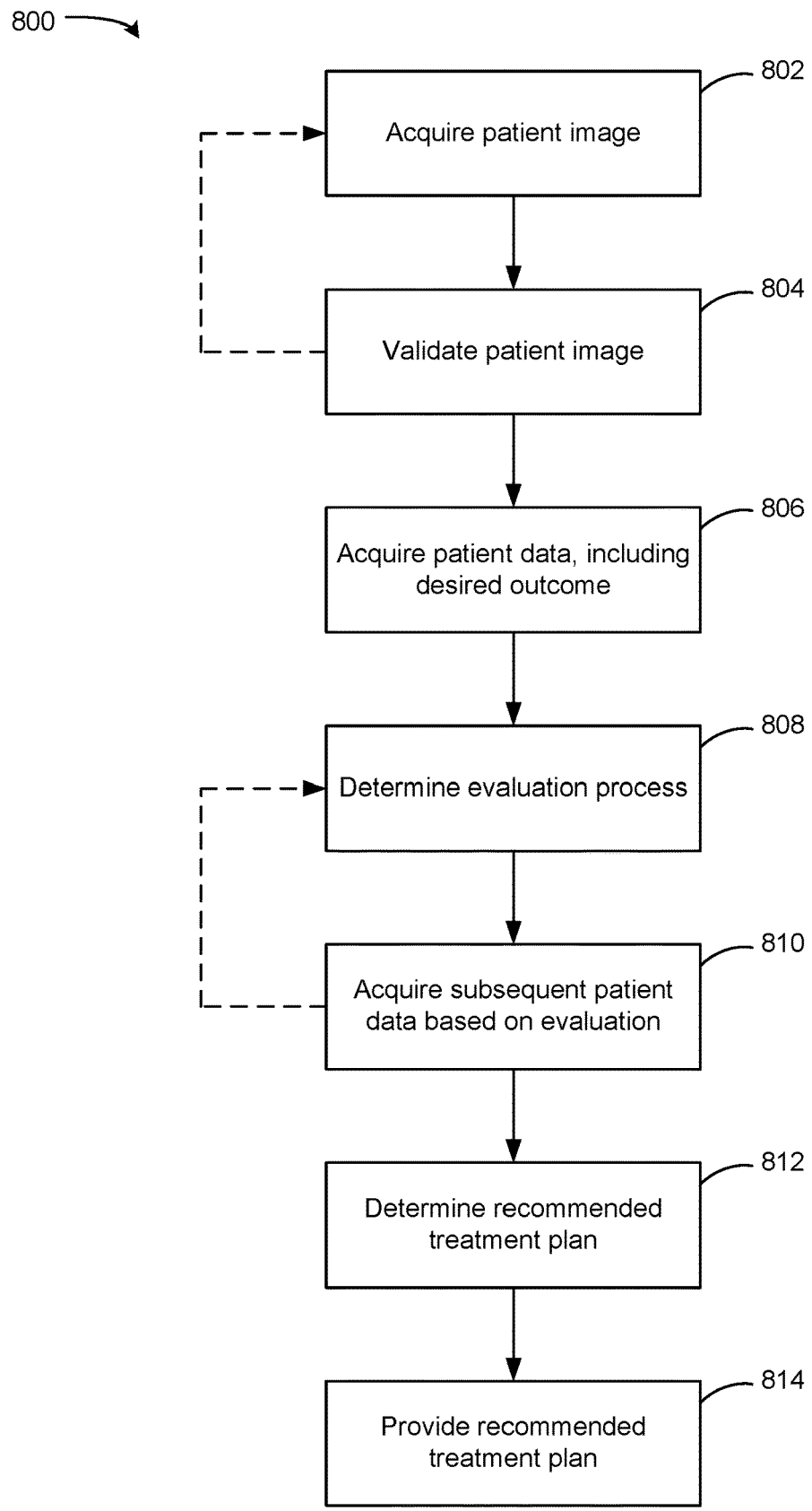
FIG. 8 is a flow diagram illustrating a method for providing customized treatment plans in accordance with some embodiments.

FIG. 8 is a flow diagram illustrating a method 800 for providing a customized treatment plan 130 to a patient, in accordance with some embodiments. The method is performed at a computing platform 100 (also referred to herein as a computer system), a local or remote image database 152, and/or a practitioner device 154. For example, instructions for performing the method are stored in the memory 102 and executed by the processor(s) 104 of the computer system 100. In some embodiments, part or all of the instructions for performing the method are stored in memory and executed by processor(s) of the practitioner device 154. In FIG. 8, dotted lines are used to indicate optional operations.

The system acquires (802) one or more images of the patient (e.g., image data 126). In some embodiments, a user interface of a display of the system 100 or device 154 displays a prompt for an image of the patient's face (or any body part undergoing cosmetic treatment). The practitioner captures the image using an imaging sensor (e.g., a camera) communicatively coupled, or capable of being communicatively coupled, to the system 100. The system receives the captured image and stores it in memory (e.g., image data 126a in memory 102). In some embodiments, the system 100 prompts the practitioner to obtain images of (i) the full face and neck in repose in three views (frontal, 45° angle, 90° angle); (ii) the full face and neck while smiling in three views (frontal, 45° angle, 90° angle); (iii) the full face and neck with the head tilted downward in three views (frontal, 45° angle, 90° angle); and/or (iv) a top-down view to assess malar region asymmetry. In some embodiments, the system 100 prompts the practitioner to obtain (i) frontal photos of the upper third of the face in repose; (ii) frontal photos of the upper third of the face with animation (e.g., frown, brow elevation, smile); (iii) oblique photos of the upper third of the face with maximum smile; (iv) photos of the lower third of the face in repose in three views (frontal, 45° angle, 90° angle); and/or (v) frontal photos of the lower third of the face with animation (frown, pursing of lips, smile).

In some embodiments, the system validates (804) the image before proceeding. Alternatively, the system validates the image after a subsequent step, or in some embodiments, does not perform a validation step. In some embodiments, the system validates the image using a validation model 148. Additionally or alternatively, the system validates the image by analyzing spatial features of particular areas of the face, such as distances, offsets, angles, and/or symmetries, and determining (e.g., based on the validation model 148)

whether the system can rely on the image in further steps in accordance with the analysis. Additionally or alternatively, the system analyzes one or more of: image resolution, pan, tilt, zoom level, subject placement, and/or light levels to determine whether the system can accurately rely on the image in further steps. In some embodiments, the system simply uses the validation model 148 to determine a validation result.

In some embodiments, if an image does not pass the validation requirement, the system prompts the practitioner to obtain another image. Optionally, the prompt includes instructions (e.g., 306) as a result of applying the validation model 148.

In some embodiments, the system prompts the practitioner to obtain another image, regardless of the validation result. For instance, certain procedures (e.g., procedures requested by a patient or recommended by a treatment plan 130) require a plurality of views of a particular area of the face, captured from different angles. In some embodiments, the system obtains a plurality of images including different views, regardless of the procedure. Alternatively, the system only obtains images including views that are necessary for the particular procedure(s) that are requested or recommended. In some embodiments, the system includes instructions for the patient to move a particular part of the face in a certain way for one or more successive images (e.g., movements such as raising the eyebrows, smiling, flexing the neck, and so forth). For these embodiments, the system 100 stores successive patient images together as image data 126 in memory 102.

Upon receiving the requisite number and type of images, the system acquires (806) additional patient data (e.g., data 128). In some embodiments, the system acquires this data before acquiring the image(s), or concurrently to acquiring the image(s). The patient data includes physical characteristics of the patient (e.g., age, gender, ethnicity), as well as patient goals, concerns, expectations, requests, and/or motivations related to cosmetic treatment. In some embodiments, the patent data includes a record of previous cosmetic procedures (e.g., surgery and/or injections), including dates and any adverse effects.

Based on the patient's desired outcomes, the system determines (808) an evaluation process. In some embodiments, the evaluation process includes customized questions (e.g., 406) and/or a physical examination, the responses and results of which are saved as additional data 128 for the patient. For example, a physical examination includes an evaluation (e.g., using the evaluation model 400) of the face and neck at rest, quality of skin (e.g., whether there is sun damage, solar lentigines, redness, rhytids, thinness, and/or presence of scars), and/or impact of previous facial procedures (e.g., surgery and/or injections). In some embodiments, the examination includes an assessment of facial symmetry while the face is at rest, including one or more of forehead and facial rhytids, eyebrow height, orbital aperture height and width, cheek bone projection, lip length and vertical height, degree of nasolabial folds (NLF), MFs, and/or jowls. In some embodiments, the examination includes an assessment of platysmal band prominence (static vs. mimetic bands) of the neck.

In some embodiments, the system acquires (810) subsequent patient data based on initial results of the evaluation. For example, subsequent patient data includes additional questions 406, and/or additionally captured images 126 for assessing the face with different expressions. In some embodiments, for additionally captured images, the system prompts the patient to manipulate the upper face (e.g., scowl, raise eyebrows, smile) and/or the lower face (e.g., kiss, frown, smile) for further evaluation. For example, the system determines how animation of these facial features impacts signs of aging.

In some embodiments, the system (e.g., evaluation model 148) assesses deficient anterior malar projection, prominent tear trough, deficient submalar fullness, elongation of white upper lip, and/or volume loss in the lips.

In some embodiments, upon obtaining additional images of the patient's face (e.g., rotated to reveal oblique and/or profile contralateral angles), the system assesses flattening of the ogee curve, elongated lid-cheek junction, flattening of the cheek regions, concavity along cheeks, heaviness/sagging of cheeks, rhytids along the cheeks, loss of definition along jaw line, presence of jowls, and/or prominence of neck bands (Grade I-IV).

In some embodiments, upon obtaining additional images of the patient's face (e.g., positioned with the chin down and eyes up), the system assesses the cheek, jowls, and lid-cheek junction, hollowness along the tear trough, the effect of the head tilt on lower facial tissues, quality of transition between lower lid and cheek, degree of lower lid fat pseudoherniation, lack of structural support along midface, extent of waviness (lines and folds) along lower face, condition of oral commissures, NLFs, MFs, and/or extent of jowls.

In some embodiments, the system determines, based on the subsequently obtained patient data, that the patient is not a good candidate for injectables but is a good candidate for plastic surgery. In some embodiments, the system determines (or helps the practitioner determine) which patients should not be treated based on their answers to certain questions (e.g., because of permanent body dysmorphic disorder, or other problems).

Based on the patient data, the system determines (812) a recommended treatment plan (e.g., treatment plan 130 using treatment model 148). For example, the treatment plan specifies a particular neuromodulator to be injected throughout dictated facial regions. In some embodiments, the system determines the dictated regions of the face based on the patient's data 128 (e.g., concerns) and the recommendations of the treatment model 148. In some embodiments, the system accounts for potential anatomical obstructions, such as arteries, veins, and nerves (e.g., using anatomical model 148 as described above). In some embodiments, the system accounts for documented and learned concepts of facial beauty (e.g., using rating model 148 as described above). Example guidelines for treatment plans are described below.

In some embodiments, the system provides (814) the recommended treatment plan via output data on a user interface of a display of the system 100 or device 154. In some embodiments, the output data includes one or more computer generated facial views (e.g., frontal, 45°, and 90° views) of partial correction outcomes and/or full correction outcomes using neuromodulators and fillers (e.g., "after" images 704 using comparison model 148).

Example Treatment Procedures and Guidance

Figure 9:
FIGS. 9-11 are diagrams of various patient images with markers provided for guidance, in accordance with some embodiments.
Figure 10:
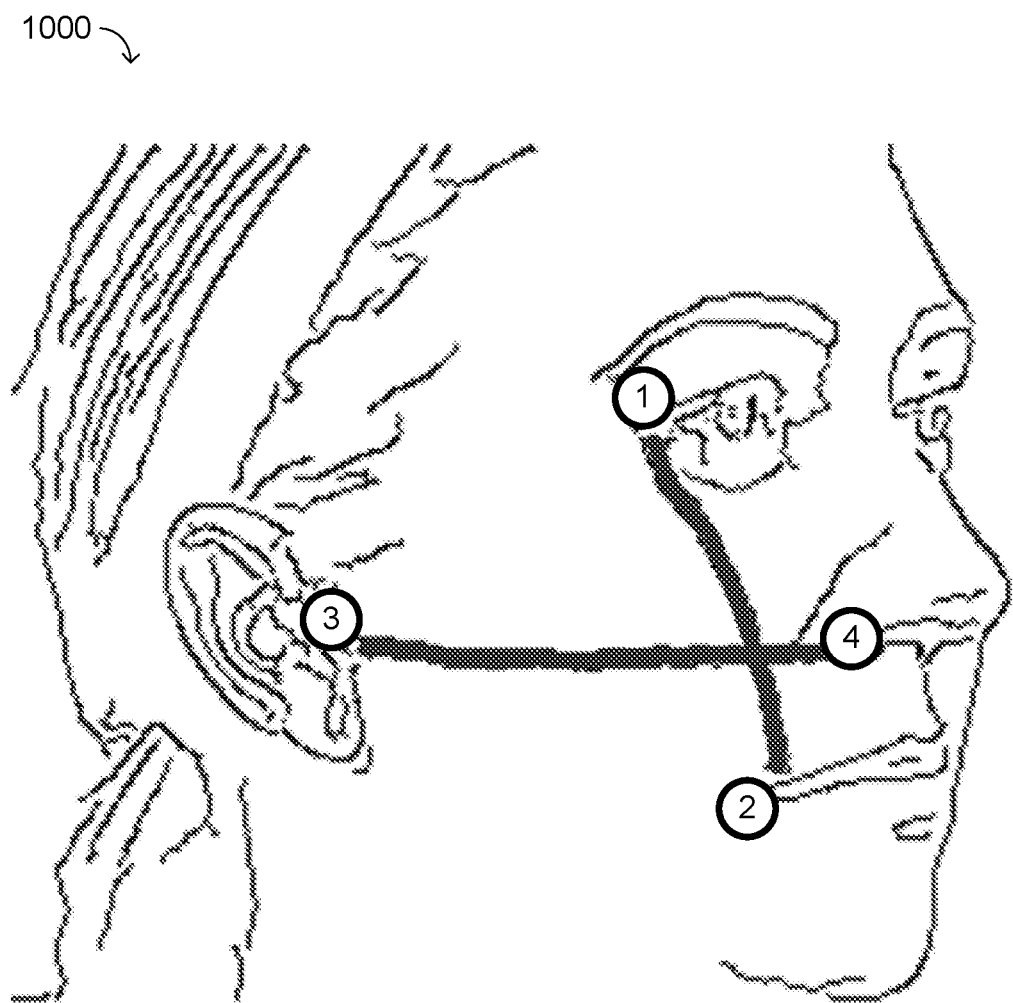
Figure 11:
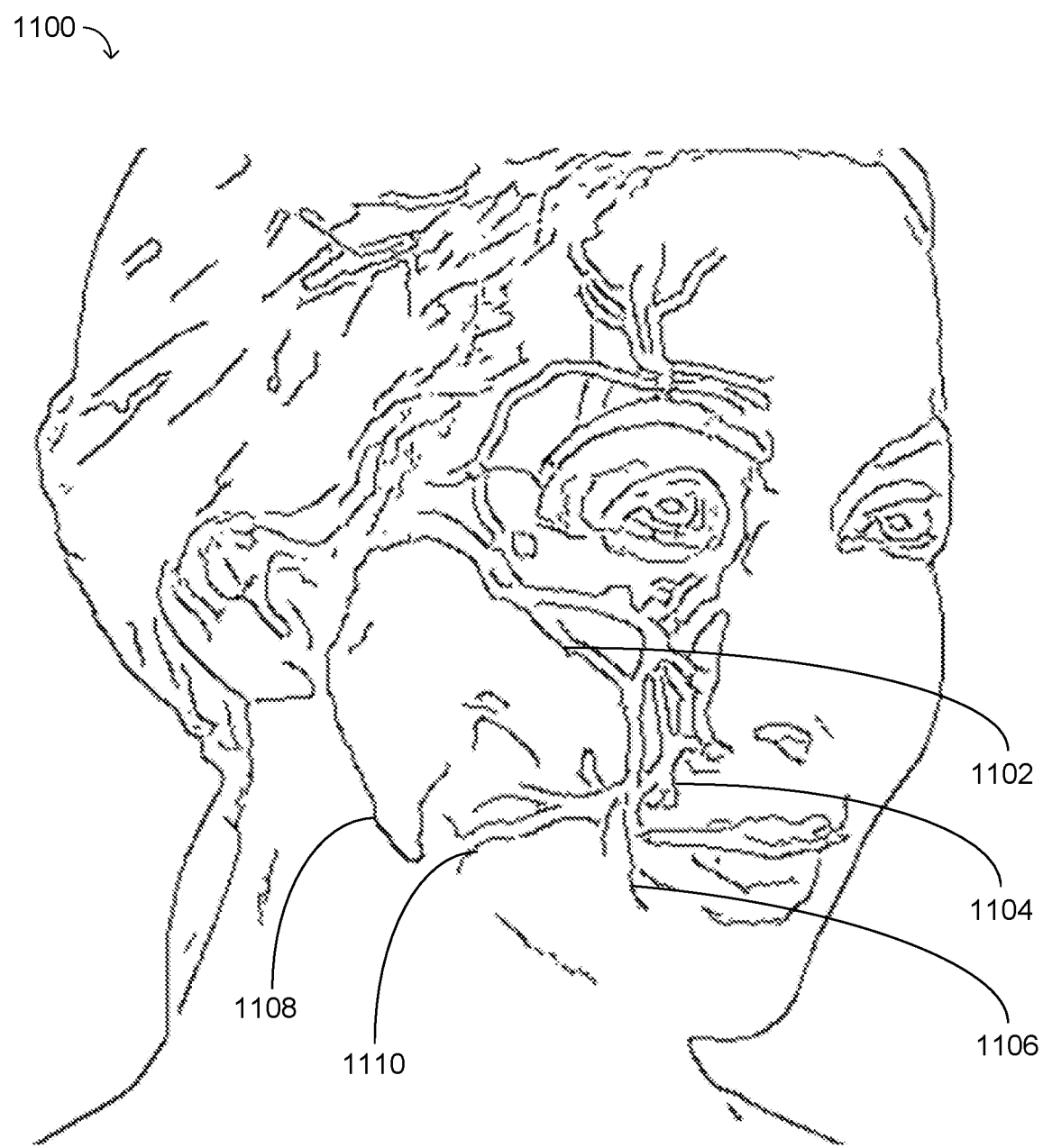

FIGS. 9-11 are diagrams of various patient images (e.g., 126) with markers provided for guidance. In some embodiments, system 100 outputs one or more of these images on a display of the system 100 or the device 154 in order to guide the practitioner during a procedure (e.g., 130).

FIG. 9 is a diagram of a patient image (e.g., 126) with a plurality of markers indicating (i) injection sites, and (ii) injection sequence. The nine markers in this example indicate injection areas in a sequence from 1 (to be injected first)

to 9 (to be injected last). However, other examples may specify alternative sequences depending on the particular treatment plan 130. The example sites and sequence shown in FIG. 9 include:

1: Lateral high zygomatic arch
2: Lateromedial zygomatic arch
3: Ateriomedial zygomatic arch
4: Submalar region
5: Nasolabial fold
6: Oral commissure
7: Marionette line
8: Upper/Lower lip volume and vermillion definition
9: Upper/Lower white lip rhytids In some embodiments, the treatment plan includes guidance for the practitioner. For example:

Inject to add volume and provide lift laterally along zygomatic arch before anteromedial and submalar regions. This (i) avoids overfilling the submalar region and (ii) optimizes the ogee curve.

After treating the midface, assess lower-face wrinkles and folds. Correcting midface volume loss often impacts the approach to treatment of the lower face.

In some embodiments, the treatment plan includes guidance for marking the face with lines (e.g., Hinderer's lines), as shown in diagram 1000 of FIG. 10. The lines in this example are marked from (1) the lateral canthus to (2) the oral commissure; and from (3) the tragus to (4) the upper alar lobule, with the lid-cheek junction being marked as an upper boundary. The four points in this example are:

1: Anchor point of the zygomatic arch, lateral to the zygomatic suture
2: The most prominent point of the zygomatic arch, medial to the zygomatic suture
3: Lateral to the infraorbital foramen
4: Submalar hollow In some embodiments, the treatment plan includes guidance for avoiding anatomical obstructions, as shown in diagram 1100 of FIG. 11. In some embodiments, the system generates this type of output image based on anatomical model 148 (FIG. 5). For example, diagram 1100 corresponds to anatomy image 504. The guidance includes markers (e.g., 1102-1110) that point out areas to avoid or areas around which to use caution. Example obstructions include the transverse facial artery, facial and angular vessels, the infraorbital neurovascular bundle, the angular artery and vein, and the parotid gland and duct.

In some embodiments, the treatment plan includes treatment goals and cautionary messages for each injection site. Referring back to FIG. 9, for example, the system provides the following guidance in accordance with some embodiments.

1: Lateral high zygomatic arch
  Anatomical treatment goals: Add supraperiosteal structural support and volume to lateral part of suborbicularis fat pad to lift cheek laterally; Establish an anchor point and fuller, rounder profile in upper cheek.
  Anatomical caution: Transverse facial artery and facial nerve run along inferior margin of zygomatic arch.
  Depth: Supraperiosteal or deep subcutaneous.

2: Lateromedial zygomatic arch
  Anatomical treatment goals: Add supraperiosteal structural support and volume to lateral part of the suborbicularis fat pad to lift and fill projection point of cheekbone; Establish transition between cheekbone and frontal cheek.
  Anatomical cautions: Transverse facial artery and facial nerve run along inferior margin of zygomatic arch.
  Depth: Supraperiosteal or deep subcutaneous.

3: Ateriomedial zygomatic arch
  Anatomical treatment goals: Restore volume to medial part of suborbicularis fat pad; Gently correct deflation in the apple of the cheek.
  Anatomical cautions: Facial and angular vessels, which pass through anteromedial cheek; Infraorbital neurovascular bundle, located deep to subcutaneous plane extending from infraorbital foramen; Angular artery and vein, located medial to this area near alar lobule. This area is not to be injected.
  Depth: Subcutaneous and superficial to infraorbital foramen.

4: Submalar region
  Anatomical treatment goals: Restore volume in deep medial cheek fat pad; Correct appearance of atrophy and smooth concavity between cheekbone and lower jaw.
  Anatomical cautions: Transverse facial artery and vein, which run along the inferior margin of the zygomatic arch at the transition between zygomaticomalar and submalar regions; Parotid gland and duct, located posteriorly in this area.
  Depth: Subcutaneous.

5: Nasolabial fold
  Anatomical treatment goals: Fill nasolabial folds
  Anatomical cautions: Facial artery and vein; Buccal nerve; Superior and inferior labial arteries; Angular artery and vein, located near superior nasolabial fold next to alar lobule; This area is not to be injected.

6: Oral commissure
  Anatomical treatment goals: Smooth oral commissures
  Anatomical cautions: Facial artery and vein; Buccal nerve; Superior and inferior labial arteries; Angular artery and vein, located near superior nasolabial fold next to alar lobule; This area is not to be injected.

7: Marionette line
  Anatomical treatment goals: Reduce marionette lines
  Anatomical cautions: Facial artery and vein; Buccal nerve; Superior and inferior labial arteries; Angular artery and vein, located near superior nasolabial fold next to alar lobule; This area is not to be injected.

8: Upper/Lower lip volume and vermillion definition
  Anatomical treatment goals: Smooth vertical lip lines
  Anatomical cautions: Facial artery and vein; Buccal nerve; Superior and inferior labial arteries; Angular artery and vein, located near superior nasolabial fold next to alar lobule; This area is not to be injected.

Additional Implementations

In addition or in the alternative to the embodiments described above, the following discussion includes additional implementations of the computing system 100.

In some embodiments, a reference image database 152 includes a plurality of facial images that the computing platform uses for comparison with one or more images of a patient's face (e.g., while using a treatment model 148 to determine a treatment plan 130). By using rating data 600, the computing platform generates treatment plans that increase patients' beauty. In some embodiments, database 152 is kept current by reviewing images of the faces of celebrities, models, and/or winners of various beauty contests in different parts of the world to maintain currency with what are considered the best up-to-date appearances.

In some embodiments, by obtaining both before and after photos (e.g., comparison data 700), the machine learning module learns with experience which outcomes are most completely and/or accurately obtained, by comparing an actual "after" image to the predicted "after" image 704.

In some embodiments, a reference image database 152 includes images depicting aging changes. The computing platform (e.g., a model 148) selects the best opportunities for changes based on the patient's age. In some embodiments, the computing platform (e.g., a model 148) identifies which changes will be best assuming the patient may have no further work done after the current session. Alternatively, the computing platform (e.g., a model 148) identifies which changes will be best assuming the patient's face will be enhanced by future treatments.

In some embodiments, the computing platform recommends a customized skin care program (e.g., in addition to the treatment data 130), including laser and/or important dermatological treatments for faces that would benefit. This aspect of the system utilizes the knowledge of other clinical specialists such as a dermatologist or aesthetician, bringing a multiple-specialist consultation to the computing platform utilization.

In some embodiments, the computing platform (e.g., a model 148) forecasts future facial degradations that might be averted through actions or different treatments (e.g., procedures 130).

Notes Regarding the Disclosure

Reference have been made in detail to various implementations, examples of which are illustrated in the accompanying drawings. In the above detailed description, numerous specific details are set forth in order to provide a thorough understanding of the invention and the described implementations. However, the invention may be practiced without these specific details. In other instances, well-known methods, procedures, components, and circuits have not been described in detail so as not to unnecessarily obscure aspects of the implementations.

It will be understood that, although the terms "first," "second," etc. may be used herein to describe various elements, these elements should not be limited by these terms. These terms are only used to distinguish one element from another. For example, a first device could be termed a second device, and, similarly, a second device could be termed a first device, without changing the meaning of the description, so long as all occurrences of the first device are renamed consistently and all occurrences of the second device are renamed consistently. The first device and the second device are both devices, but they are not the same device.

The terminology used herein is for the purpose of describing particular implementations only and is not intended to be limiting of the claims. As used in the description of the implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific implementations. However, the illustrative discussions above are not intended to be exhaustive or to limit the invention to the precise forms disclosed. Many modifications and variations are possible in view of the above teachings. The implementations were chosen and described in order to best explain the principles of the invention and its practical applications, to thereby enable others skilled in the art to best utilize the invention and various implementations with various modifications as are suited to the particular use contemplated.

What is claimed is:

1. An electronic computer system, comprising:
   one or more processors; and
   memory storing one or more programs for execution by the one or more processors, the one or more programs comprising instructions for:
   obtaining an input image of a face of a user;
   comparing, using a pattern recognition process, image data of the input image to corresponding image data of a plurality of reference images, wherein each of the plurality of reference images includes a face of an individual other than the user;
   obtaining, based on a result of the comparing, supplemental information associated with one or more additional characteristics of the face; and
   determining, based on the input image, the comparing of the image data of the input image to the corresponding image data of the plurality of reference images, and the supplemental information:
   (i) an injecting agent and an amount or unit of the injecting agent;
   (ii) a plurality of injection locations for the specific injecting agent; and
   (iii) an injection sequence associated with the plurality of injection locations; and
   displaying the injecting agent, the amount or unit of the injecting agent, the plurality of injection locations, and the injection sequence on a user interface of the electronic computer system.

2. The electronic computer system of claim 1, wherein the image data of the input image represent physical features of the face that are detectable in the input image.

3. The electronic computer system of claim 1, wherein the one or more additional characteristics include gender and/or age of a patient to which the face belongs.

4. The electronic computer system of claim 1, wherein the one or more additional characteristics include a physical condition associated with an aspect of the face, wherein the physical condition is undetectable in the input image.

5. The electronic computer system of claim 1, wherein obtaining supplemental information associated with one or more additional characteristics of the face comprises:
matching, based on the comparing, the input image with one or more reference images;
determining, based on the matching, a first type of information classified as necessary for determining the injecting agent, the plurality of injecting locations, and the injection sequence; and
providing a prompt on the user interface for obtaining the supplemental information based on the first type of information.

6. The electronic computer system of claim 1, wherein:
the pattern recognition process uses a model refined by unsupervised or adversarial training, wherein inputs of the model include the plurality of reference images, and input labels of the model include treatment plans comprising injecting agents, injection locations, and injection sequences corresponding to respective reference images of the plurality of reference images;
comparing the one or more aspects of the input image to corresponding aspects of the plurality of reference images includes matching the input image to a first reference image of the plurality of reference images using the model; and
the injection agent, the plurality of injection locations, and the injection sequence determined based on the comparing correspond to the first reference image.

7. The electronic computer system of claim 1, wherein:
the pattern recognition process uses a model refined by unsupervised or adversarial training, wherein inputs of the model include the plurality of reference images, and input labels of the model include one or more evaluation questions corresponding to respective reference images of the plurality of reference images; and
obtaining the supplemental information includes (i) matching the input image to a first reference image of the plurality of reference images using the model, and (ii) providing a prompt on the user interface for obtaining the supplemental information based on one or more evaluation questions corresponding to the first reference image, wherein the prompt includes the one or more evaluation questions.

8. A method, comprising:
at an electronic computer system including one or more processors and memory storing one or more programs for execution by the one or more processors:
obtaining an input image of a face of a user;
comparing, using a pattern recognition process, image data of the input image to corresponding image data of a plurality of reference images, wherein each of the plurality of reference images includes a face of an individual other than the user;
obtaining, based on a result of the comparing, supplemental information associated with one or more additional characteristics of the face; and
determining, based on the input image, the comparing of the image data of the input image to the corresponding image data of the plurality of reference images, and the supplemental information:
(i) an injecting agent and an amount or unit of the injecting agent;
(ii) a plurality of injection locations for the specific injecting agent; and
(iii) an injection sequence associated with the plurality of injection locations; and
displaying the injecting agent, the amount or unit of the injecting agent, the plurality of injection locations, and the injection sequence on a user interface of the electronic computer system.

9. The method of claim 8, wherein the image data of the input image represent physical features of the face that are detectable in the input image.

10. The method of claim 8, wherein the one or more additional characteristics include gender and/or age of a patient to which the face belongs.

11. The method of claim 8, wherein the one or more additional characteristics include a physical condition associated with an aspect of the face, wherein the physical condition is undetectable in the input image.

12. The method of claim 8, wherein obtaining supplemental information associated with one or more additional characteristics of the face comprises:
matching, based on the comparing, the input image with one or more reference images;
determining, based on the matching, a first type of information classified as necessary for determining the injecting agent, the plurality of injecting locations, and the injection sequence; and
providing a prompt on the user interface for obtaining the supplemental information based on the first type of information.

13. A non-transitory computer readable storage medium storing one or more programs configured for execution by a computer system, the one or more programs including instructions for:
obtaining an input image of a face of a user;
comparing, using a pattern recognition process, image data of the input image to corresponding image data of a plurality of reference images, wherein each of the plurality of reference images includes a face of an individual other than the user;
obtaining, based on a result of the comparing, supplemental information associated with one or more additional characteristics of the face; and
determining, based on the input image, the comparing of the image data of the input image to the corresponding image data of the plurality of reference images, and the supplemental information:
(i) an injecting agent and an amount or unit of the injecting agent;
(ii) a plurality of injection locations for the specific injecting agent; and
(iii) an injection sequence associated with the plurality of injection locations; and
displaying the injecting agent, the amount or unit of the injecting agent, the plurality of injection locations, and the injection sequence on a user interface of the electronic computer system.

14. The non-transitory computer readable storage medium of claim 13, wherein the image data of the input image represent physical features of the face that are detectable in the input image.

15. The non-transitory computer readable storage medium of claim 13, wherein the one or more additional characteristics include gender and/or age of a patient to which the face belongs.

16. The non-transitory computer readable storage medium of claim 13, wherein the one or more additional characteristics include a physical condition associated with an aspect of the face, wherein the physical condition is undetectable in the input image.

17. The non-transitory computer readable storage medium of claim 13, wherein obtaining supplemental information associated with one or more additional characteristics of the face comprises:
- matching, based on the comparing, the input image with one or more reference images;
- determining, based on the matching, a first type of information classified as necessary for determining the injecting agent, the plurality of injecting locations, and the injection sequence; and
- providing a prompt on the user interface for obtaining the supplemental information based on the first type of information.

\* \* \* \* \*